United States Patent
Choye et al.

(10) Patent No.: US 11,730,539 B2
(45) Date of Patent: *Aug. 22, 2023

(54) METHOD AND APPARATUS FOR DIRECTIONAL SKIN TIGHTENING

(71) Applicant: LUMENIS LTD., Yokneam (IL)

(72) Inventors: Raymond Choye, Belmont, CA (US); Lior Greenbaum, Yokneam Ilit (IL)

(73) Assignee: LUMENIS BE LTD., Yokneam (IL)

( * ) Notice: Subject to any disclaimer, the term of this patent is extended or adjusted under 35 U.S.C. 154(b) by 11 days.

This patent is subject to a terminal disclaimer.

(21) Appl. No.: 16/693,235

(22) Filed: Nov. 23, 2019

(65) Prior Publication Data
US 2022/0265348 A1 Aug. 25, 2022

Related U.S. Application Data (63) Continuation of application No. 15/423,619, filed on Feb. 3, 2017, now Pat. No. 10,524,863.

(60) Provisional application No. 62/291,796, filed on Feb. 5, 2016.

(51) Int. Cl.
A61B 18/20 (2006.01)
A61B 18/00 (2006.01)

(52) U.S. Cl.
CPC .... *A61B 18/203* (2013.01); *A61B 2018/0047* (2013.01); *A61B 2018/00452* (2013.01); *A61B 2018/00577* (2013.01); *A61B 2018/00589* (2013.01); *A61B 2018/00619* (2013.01); *A61B 2018/2015* (2013.01)

(58) Field of Classification Search
CPC ........ A61B 18/203; A61B 2018/00452; A61B 2018/0047; A61B 2018/00577; A61B 2018/00589; A61B 2018/00619; A61B 2018/2015
See application file for complete search history.

(56) References Cited

U.S. PATENT DOCUMENTS

| | | | |
|---|---|---|---|
| 2008/0172047 A1* | 7/2008 | Altshuler | A61H 39/002 606/9 |
| 2015/0150629 A1* | 6/2015 | Anderson | A61B 17/083 606/9 |
| 2015/0202007 A1 | 7/2015 | Manstein | |

FOREIGN PATENT DOCUMENTS

| | | |
|---|---|---|
| WO | 2008049905 | 5/2008 |
| WO | 2008083305 | 7/2008 |
| WO | 2009070677 | 6/2009 |
| WO | 2009090433 | 7/2009 |

(Continued)

OTHER PUBLICATIONS

Search Report—Corresponding European Application No. 17155757.2, dated Jan. 22, 2018, 7 pages.

*Primary Examiner* — Mallika D Fairchild
*Assistant Examiner* — Shreya Anjaria
(74) *Attorney, Agent, or Firm* — Isus Intellectual Property PLLC; Anthony Jason Mirabito (57) ABSTRACT

A cosmetic method of directionally tightening human skin tissue includes providing an ablative laser source and a non-ablative laser source, then using the ablative laser source to form one or more overlapping circular shaped microchannels in the skin tissue; the overlapping microchannels formed have a longitudinal dimension larger than their cross dimension; then, using the non-ablative laser source to weld the microchannels, whereby the welding causes the skin tissue to tighten.

9 Claims, 13 Drawing Sheets

(56) References Cited

FOREIGN PATENT DOCUMENTS

| | | |
|---|---|---|
| WO | 201408481 | 1/2014 |
| WO | 2014040015 | 3/2014 |

\* cited by examiner

LASER HOMOGENOUS FRACTION
(NON-DIRECTION)

FIG.9A

APPLYING SHRINKING PLASTER

FIG.9B

DRAWING HOT "COAGULATIVE" LINE
ON THE SHRINKING PLASTER

FIG.9C

CREATING DIRECTIONAL TIGHTENING
DUE TO PLASTER SHRINKING

METHOD AND APPARATUS FOR DIRECTIONAL SKIN TIGHTENING

RELATED APPLICATION

This application is a continuation application of U.S. application Ser. No. 15/423,619, filed Feb. 3, 2017, and claims priority to U.S. provisional application Ser. No. 62/291,796, filed Feb. 5, 2016, the entire contents of which are herein incorporated by reference.

BACKGROUND

Present day non-invasive skin tightening techniques only deliver small, millimeters of improvement. By contrast, in an invasive procedure, such as a facelift, typically larger, centimeters of improvement are experienced. Directional skin tightening is commonly known in that one can shape the skin with a skin compression technique in which the skin would generally be expected to hold its shape.

SUMMARY OF THE PRESENT INVENTION

Herein it is suggested achieving directional shrinkage of the skin by combining two different mechanism of actions induced by two lasers sources: an ablative laser (such as, for example, an Erbium laser working at a wavelength of about 2.9 µm (about 2940 nm) or a CO2 laser working at wavelength of about 10.6 µm (about 10,600 nm)) with subsequent application of heating through a non-ablative laser (such as, for example, a laser operating at about a range of wavelengths from about 1400 nm to about 1,565 nm). The idea behind the concept is induce a sequence of fractional ablative holes in skin using the ablative laser, to compress the holes, thus reducing the linear dimension of the skin in the direction of the compression, which will subsequently be welded closed by the non-ablative laser and then held or otherwise maintained in place in this reduced dimension for the duration of the healing process, thus providing a directional tightening effect. In addition to light energy in the above wavelengths for the non-ablative heating, other methods may be used, such as RF energy or another light energy source which selectively absorbs water or hemoglobin at sub-ablative energy dosages. Other light-based wavelengths include: 500-600 nm, 980-2000 nm or Intense Pulsed Light (IPL) energy filtered to correspond to the foregoing wavelengths.

In an aspect, a cosmetic method of directionally tightening human skin tissue includes: (a) providing an ablative laser source and a non-ablative laser source; (b) using the ablative laser source to form one or more overlapping circular shaped microchannels in the skin tissue; the overlapping microchannels formed having a longitudinal dimension larger than their cross dimension; and (b) using the non-ablative laser source to weld the microchannels, whereby the welding causes the skin tissue to tighten.

In another aspect, the cosmetic method further includes the step of squeezing or stretching the skin tissue in a longitudinal direction or in a cross direction or both. In the present cosmetic method, step (b) takes place before step (c) or step (c) takes place before step (b) or the sequence of steps is: (c) followed by (b) followed by (c). Further, the step of squeezing or stretching is performed before step (b) or the step of squeezing or stretching is performed after step (b) or the step of squeezing or stretching is performed after step (c).

In a further aspect, the step of squeezing or stretching is performed with a mechanical squeezer or stretcher. The skin tissue may be held in a squeezed or stretched condition for a period of time sufficient to weld the microchannels. The cosmetic method may further include the step of providing an isotropic or anisotropic polymer sheet, placing the sheet on the skin tissue surface; performing step (b) and then step (c) such that the polymer sheet shrinks one of isotropically or anisotropically. In an alternative embodiment, the skin tissue is treated with the ablative then the non-ablative laser(s) and, once welded, the polymer sheet is placed over the skin tissue for a period of time to maintain the position for sufficient time to assure that the weld "takes".

In yet another aspect, a cosmetic method of directionally tightening human skin tissue includes: providing an ablative laser source and a non-ablative laser source; using the ablative laser source to form one or more microchannels in the skin tissue; using the non-ablative laser source to weld the microchannels, whereby the welding causes the skin tissue to tighten in the cross direction. It may include the further step of squeezing or stretching the skin tissue in the cross direction.

In yet a further aspect, the method of the present invention, the wavelength of the ablative laser may be about 10,600 nm or about 2940 nm and the wavelength of the non-ablative laser may range from about 1400-1565 nm.

In another aspect, in the cosmetic method, the mechanical squeezer or stretcher comprises a body portion, the body portion having a plurality of arms, wherein the arms have end portions which are movable towards and away from one another, further comprising the steps of contacting the skin tissue with the end portions of the arms and manipulating the end portions in contact with the skin tissue to either move towards one another or move away from one another, thereby either squeezing or stretching the skin tissue. The mechanical squeezer or stretcher may be mounted on the distal portion of a laser device In a further aspect, the skin tissue treated is one or more wrinkles or other imperfections and the step of squeezing or stretching is across the one or more wrinkles or other imperfections along the long axis of the one or more wrinkles or other imperfections.

DETAILED DESCRIPTION OF THE PRESENT INVENTION

Figure 1:
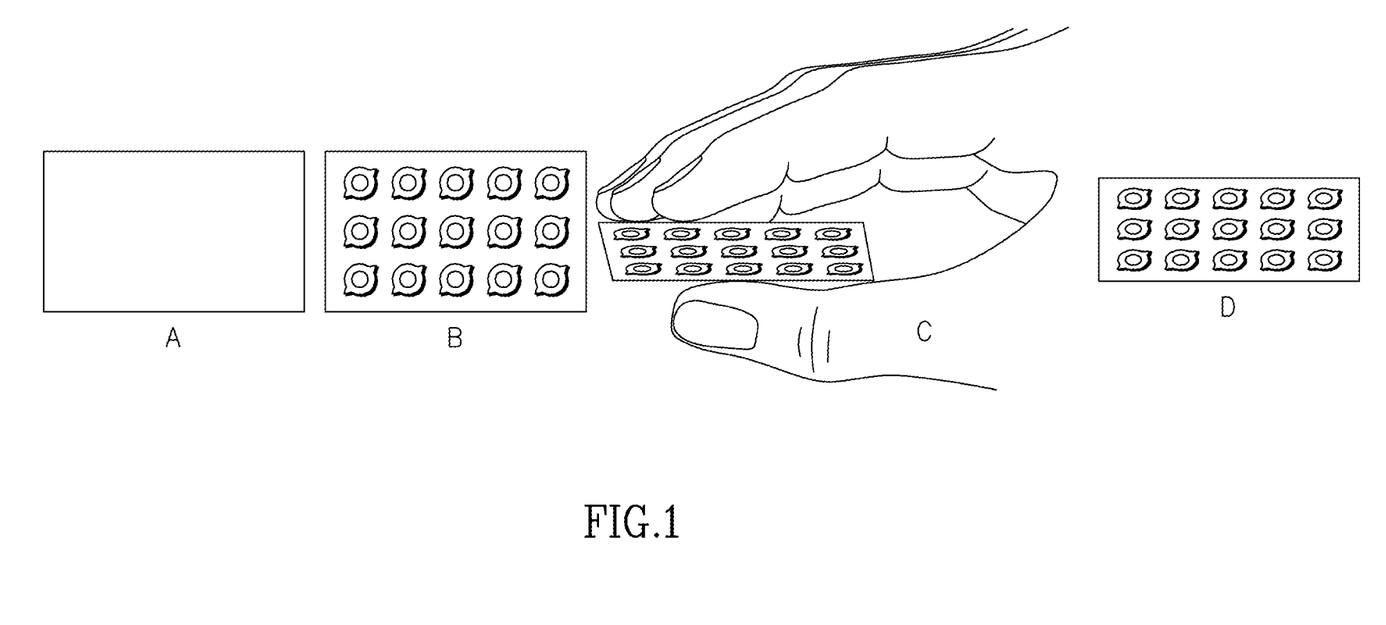
FIG. 1 illustrates the steps in the formation of welded microchannels in the present invention.

The welding discussed above may be achieved in a directional manner, by way of example only, by an operator physically pushing, squeezing or otherwise manipulating the skin in one direction of an array of fractional ablated holes, and then applying the second laser source to weld and hold this shape, as may be see in FIG. 1. Several studies have shown that laser assisted tissue bonding (LTB) offers a fast and efficient method for full-thickness macroscopic incision closure, which diminishes scar formation. Examples in the literature include the following:

Fried N M, Walsh J T Jr. Laser skin welding: in vivo tensile strength and wound healing results. Lasers Surg Med. 2000; 27(1):55-65; Simhon D, Halpern M, Brosh T, Vasilyev T, Ravid A, Tennenbaum T, Nevo Z, Katzir A. Immediate tight welding of skin incisions using an innovative temperature-controlled laser soldering device: in vivo study in porcine skin. Ann Surg. 2007 February; 245 (2):206-13; Ahmed A. Abbood Human Skin Wound Welding Using 980 nm Diode Laser: an in Vitro Experimental Study. Iraqi J. Laser, Part B, Vol. 11, pp. 9-20 (2012)

While traditional full-thickness macroscopic incisions are characterized by the full separation of opposing tissue from both sides of the cut and leaving a macroscopic void volume between them, LTB may be basically subdivided into 2 main sub-phases differing in their mechanism of action: 1) photochemical tissue bonding (PTB) and 2) photothermal tissue bonding. The latter can be further subdivided into 2 different aspects: laser tissue welding (LTW) and laser tissue soldering (LTS). LTW refers to the introduction of concentrated laser energy to the opposed wound margins that causes their initial liquefaction, followed by fusion of the two edges, whereas LTS uses an additional component known as a "solder" (see above references). The present invention generally relates to the LTW type of mechanism in order to directionally tighten the skin in the desired shape.

In connection with fractional laser skin treatment, which is an aspect of the present invention, a study was made to evaluate the feasibility of directional skin tightening, using the fractional ablative CO2 laser (10,600 nm) and subsequently the non-ablative laser (1,565 nm) on fresh harvested porcine skin (ex-vivo model). Porcine skin is highly similar to the skin anatomy and physiology of humans.

This study was designed to prove the concept of inducing directional skin tightening by combining two lasers sources, working in different mechanisms of action, welding the holes closed in the compressed direction.

The experimental setups evaluated by this study are described in Table 1 below:

TABLE 1

Description of laser setups

| Setup | Ablative laser (10 μm) | Non-ablative laser (1,565 nm) |
|---|---|---|
| 1 | SuperPulse<br>AcuScan 120 DeepFX<br>10 mj<br>10 × 10 mm at density of 10%<br>Expected diameter of ablative zone: 120 μm | ResurFX (M22) & scanner<br>No sapphire (without topical cooling)<br>Pulse E: 30 mj<br>Pulse width: 2.5 ms<br>10 × 10 mm at density of 450/cm$^2$<br>Expected diameter of coagulative zone: 100 μm<br>This setup was evaluated in single and double-pass |
| 2 | SuperPulse<br>AcuScan 120 DeepFX<br>10 mj<br>10 × 10 mm at density of 10%<br>Expected diameter of ablative zone: 120 μm | ResurFX (M22) & free fiber (no scanner)<br>No sapphire (without topical cooling)<br>Pulse E: 13 W<br>Pulse width: continuous 10 s all over the whole area<br>Expected diameter of coagulative zone: 100 μm<br>This setup was evaluated in single and double-pass |

The study was designed to evaluate the histological effect of combined treatments of ablative and non-ablative laser energies to induce directional skin tightening effects. The treatment included the following three steps: (1) Fractional ablative treatment with a CO2 laser. (2) The treated area was then manually squeezed in the desired direction and held in that position until completion of step (3). (3) The squeezed/compressed tissue was welded with the non-ablative laser.

Figure 2:
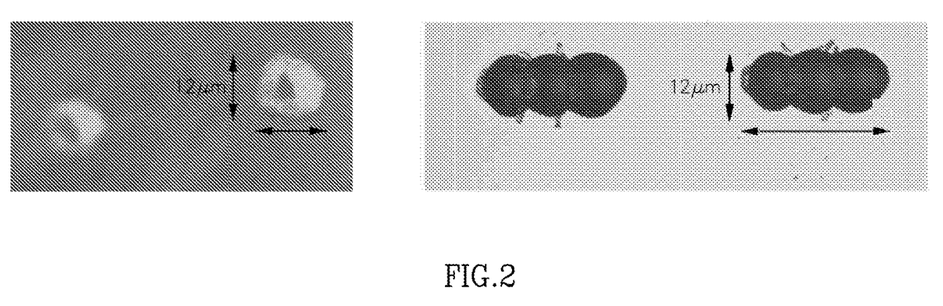
FIG. 2 illustrates one method by which oval-shaped microchannels are produced in the present invention.

In this in-vivo study, fractional oval holes were ablated and evaluated. One technique to create such oval holes is to closely space the formation of the (normally) circular holes or microchannels so that the edges of one hole overlap in a longitudinal direction with the hole or holes immediately preceding it, as can be seen in FIG. 2. Other techniques of ablating elongated microchannels or compressing circular microscopic channels to make them oval are known in U.S. Pat. No. 7,942,153 and US application No. 2015/0150629 respectively.

However, in the present invention, the combinational use of a fractional ablative laser followed by applying directional force across the pattern of fractional holes and a non-ablative laser is utilized to form and then weld the microchannels in a required orientation. For example, single microchannels of a 120 μm diameter may be combined to produce an elongated "micro-cut" that is approximately 300 um in length, again as may be seen in FIG. 2. In addition, a guiding mechanism may be employed under the control of a suitable programmable controller which "remembers" the positions of the microchannels and directs the non-ablative laser to those microchannels or in the vicinity of those microchannels. In an alternative arrangement, the non-ablative laser may not be directed to the microchannels, as above, but rather may be activated in the general area in which the microchannels were formed.

The elongated microchannels or micro-cuts (as they hereinafter may be referred to) discussed above may be, of course of any length, width, depth, or orientation suitable for the particular application. For example, a plurality of elongated micro-cuts may be arranged with their long axes in parallel with one another or may be arranged randomly with respect to one another. Also, the long axes may be positioned on the skin tissue surface parallel to, for example, the long axis of a wrinkle or wrinkles or may be positioned perpendicular to the long axis of a wrinkle or wrinkles. In a treatment of facial imperfections, the elongated micro-cuts may vary greatly in their direction and orientation with respect to one another and with respect to skin surface wrinkles and other imperfections. Microchannels may be any pattern of discrete circular holes distributed homogeneously or non-homogenously, partially overlapped or without any overlap, on a skin area where a directional force or a directional tightening is required such as, for example, along a wrinkle to be stretched so as to cause the wrinkle to completely or mostly disappear.

The purpose of the directional compression is to close the void caused by the ablation, bringing the margins of the micro-cuts together prior to their welding. The direction of the compression may be in any orientation relative to the elongated micro-cuts, along its short or long axis (such as shown in FIGS. 1A-D) or along the short axis (not shown) in order to achieve different desired effects.

The capability of directional tissue welding using a non-ablative coagulative laser source which followed the forming of an ablated fractional pattern and its directional compression, demonstrated that the margins of the micro-cuts were attached to each other. Known in the prior art is the use of non-ablative laser directed into ablated holes to coagulate the content therein in order to reduce the hole depth and healing time. This technique is disclosed, for example, in US application no. 20150202007. Directional compressing and directional welding of the margins of micro-cuts in order to achieve directional skin tightening are aspects of the present invention.

Figure 3:
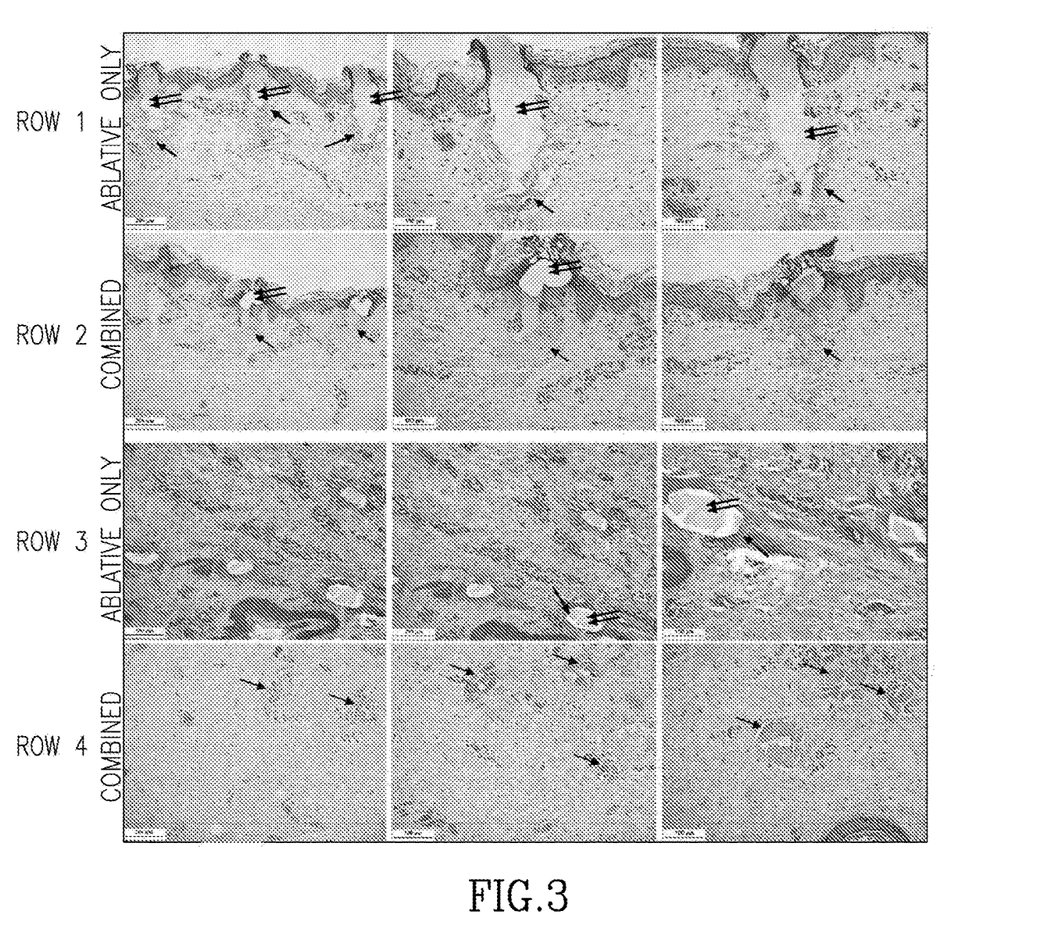
FIG. 3 illustrates photographically the results of a study to implement the method of operating the dual laser sources in the present invention.
Figure 4:
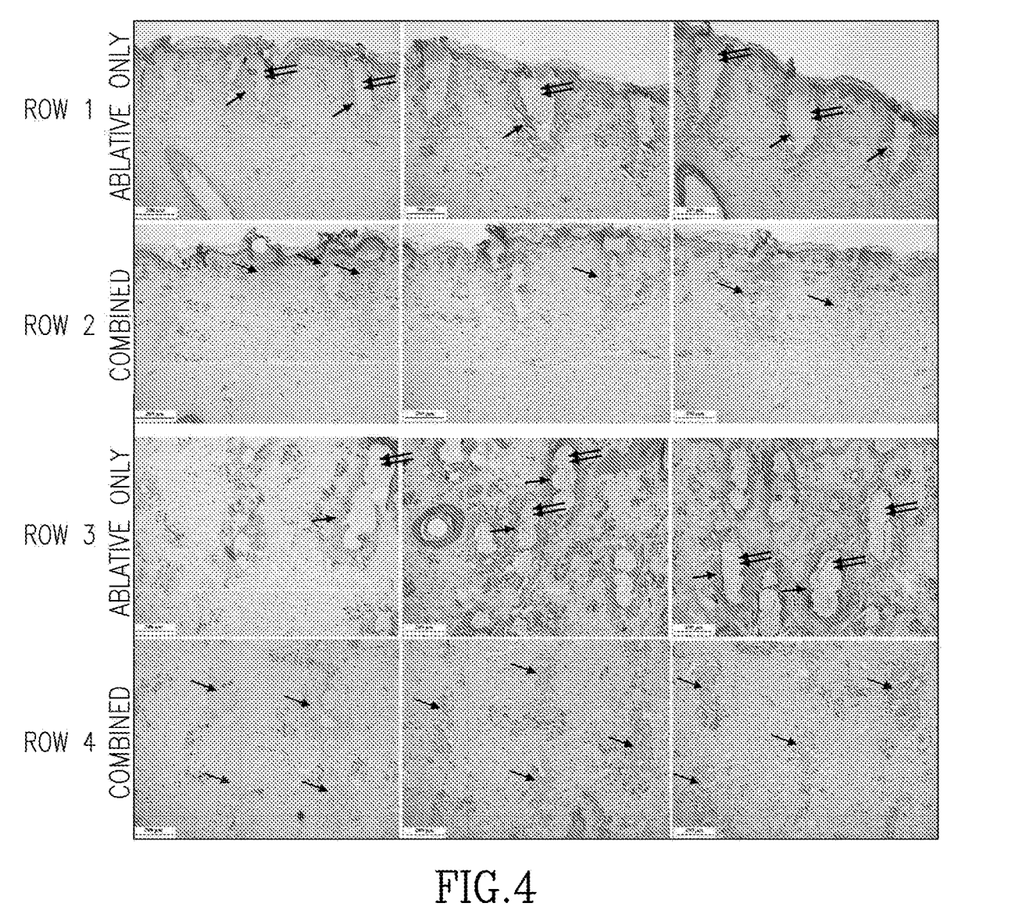
FIG. 4 illustrates photographically the results of a study to implement the method of operating the dual laser sources of the present invention.

Treatments with the ablative laser in these experiments resulted in ablative holes with a diameter of ~120 µm. This could be detected by both binocular microscopy and histologically. FIGS. 3 and 4 illustrate histological comparisons between ablative only treatments and combined treatments of ablating-squeezing-welding. The upper two rows 1 and 2 in each of FIGS. 3 and 4 provide perpendicular cross-section views of the skin sample and the lower two rows provide a horizontal cross-section view at a depth of up to 60 µm from sample skin surface.

After compression of the skin tissue, the goal was to apply the non-ablative laser to the compressed lesions to perform the welding of the lesion closed. An attempt at a high density exposure was thought to insure a higher probability to align with many of the ablated lesions and an additional set up attempted to expose the area with a large spot fiber over the entire surface area for a completely confluent treatment making sure to expose over the ablated lesions.

As can be seen in FIG. 3 and in FIG. 4, the margins of the ablated zones were surrounded by a thin rim of coagulation area marked with single arrows. Ablated areas are marked in the figures with double arrows. In contrast to the macro voids created by full thickness macroscopic incision mentioned above which can be welded or soldered according to the prior art, fractional ablated microchannels provide micro-reservoirs to hold and contain secretions from adjacent tissues such as, for example, capillary blood or extracellular fluid as well as cellular fluid originating from ruptured cells along the margins of the holes.

These fluid components contain, at least partially, proteinic material and chromophores such as hemoglobin. Therefore, the bonding of the microchannels or micro-cuts by a non-ablative laser may be a combination of LTB, LTW and LTS. The amount of fluid secreted into a micro-cut is a function, among other things, of the internal holes' surface. Due to the fractional nature of the ablative step in this directional tightening treatment, the area of a microchannel surface over the microchannel volume is much higher than in the case of a full thickness incision. Moreover, a full thickness incision does not form a closed container which may hold and contain fluids from adjacent tissue or alternatively may create an overflow of bleeding should a blood vessel be cut. Therefore, the microchannel diameter of the ablated holes may be selected by the user to affect the amount of fluid to be secreted into the holes. The Thermal Affected Zone (TAZ) created along the margins of the ablated holes may be controlled by the user as disclosed in US application No. 2011077627 which is incorporated herein by reference in its entirety. A thicker TAZ may reduce the amount of fluid accumulated in a microchannel while a thinner TAZ may allow more fluid to be drained through the thinner coagulated area.

Figure 5:
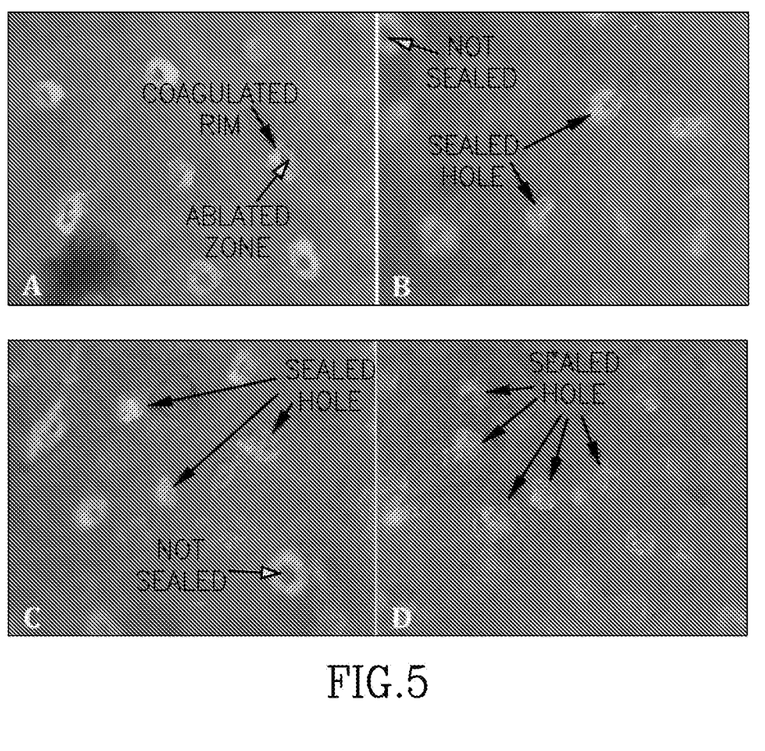
FIG. 5 illustrates photographically the welding of microchannels formed in accordance with the present invention.

Referring now to FIG. 5, this figure provides a top view of a skin surface treatment of the present invention under binocular microscopy. Part A represents the result right after ablation with a CO2 laser. Parts B and C represent results following an additional non-ablative treatment, performed in one pass with a 1565 nm laser. Part D is similar to Parts B and C, but with two passes of the non-ablative laser. The non-welded ("unsealed" as marked in the photographs) holes are seen and may be expected as the non-ablative laser was applied with the ablation zone randomly.

Figure 6:
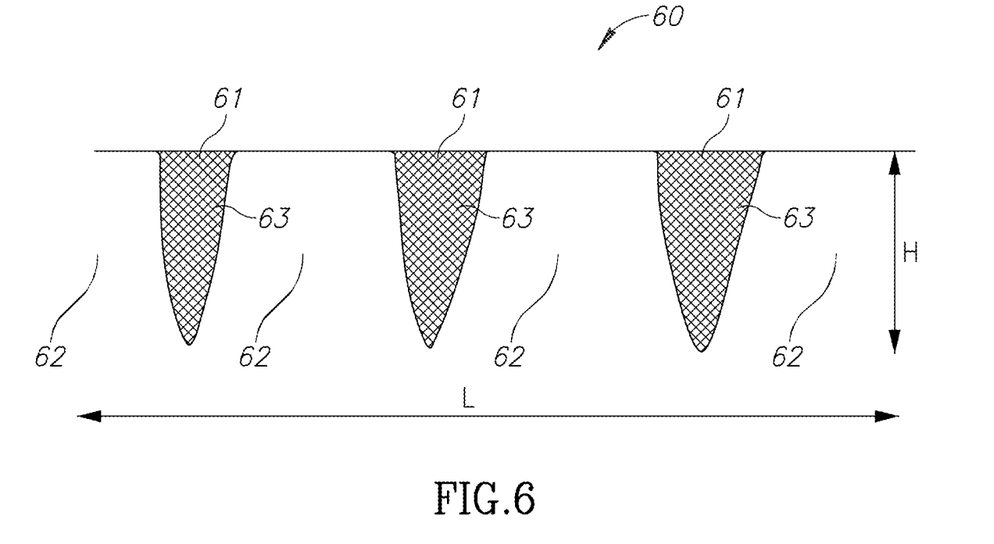
FIGS. 6 and 7 illustrate cross-sectional and top views respectively of ablated microchannels.
Figure 7:
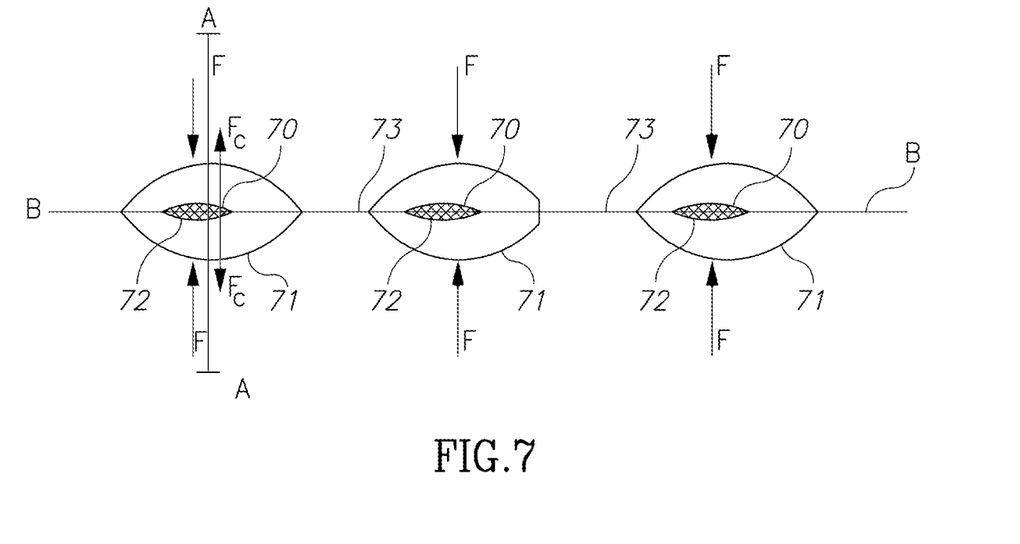

Referring now to FIG. 6, that figure shows a skin cross section 60 having ablated microchannels 61 and intact tissue areas 62 between them. Areas 63 are part of the microchannel's internal surfaces shown in this cross section. Skin cross section 60 defines a fractionated incision plane, perpendicular to skin surface, having a length L and a height H. A fractionated incision plane consists of ablated strips defined by ablated microchannels 61 and the intact tissue areas 62 between them. Another aspect of the present invention is a method to create at least one fractionated incision plane using an ablative fractional laser, and then compressing the at least one fractionated incision plane with a mechanical force F which is approximately perpendicular to the fractionated incision plane, as seen in FIG. 7 from a top view, to close microchannels 70. This is followed by providing targeted non-ablative laser spots 71 which are configured to bond together the compressed sides of at least some of microchannels 70.

In addition, multiple parallel fractionated incision planes may be created across the skin. Welding a microchannel having a diameter of D, for example, creates a displacement of about D/2 of tissue from each side across the bonding line 72. Therefore, by creating multiple fractionated incision planes one can obtain accumulated directional tightening proportional to the product of D/2 and number of planes. The length of bonding line 72 is proportional to the product of $\pi$ and the microchannel diameter. Once the external mechanical force F is removed after bonding, bonded microchannels 71 tighten the skin along line A-A. At the same time, counterforces Fc acting on bonding lines 72 in a direction tend to reopen the bonded microchannels. The present invention provides bonding strength sufficient to overcome the load encountered by counter force Fc. The fractionated incision plane is characterized, among other things, by the ratio of the length of bonding lines 72 over intact lines 73 across line B-B. The larger this ratio is, the higher the counter force Fc and the stronger the bonding force required.

Figure 8:
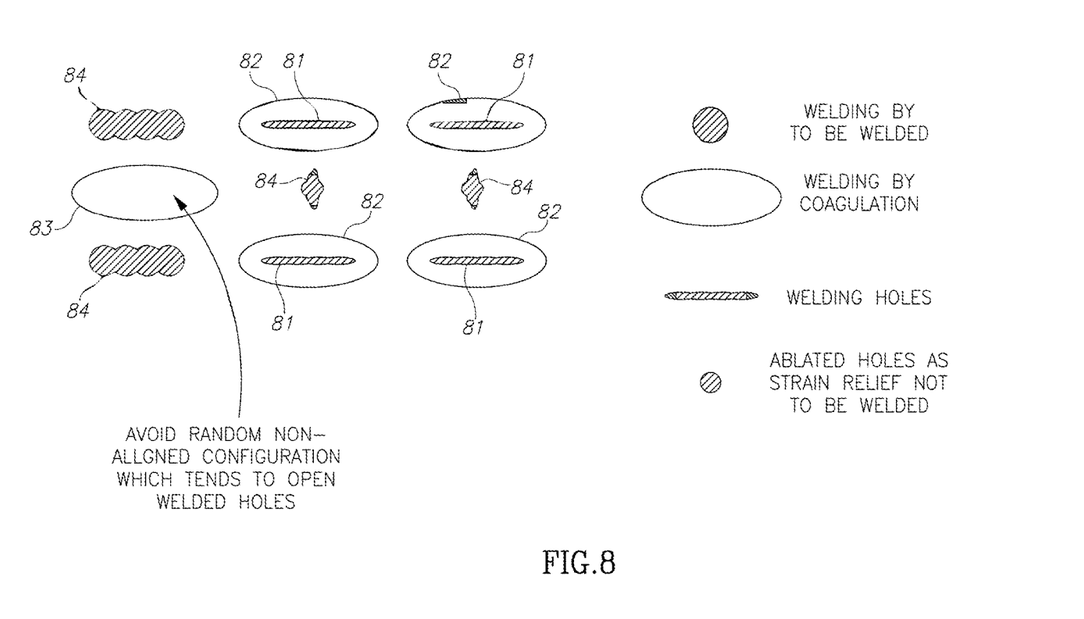
FIG. 8 illustrates compressed and welded micro-cuts.
Figure 9A:
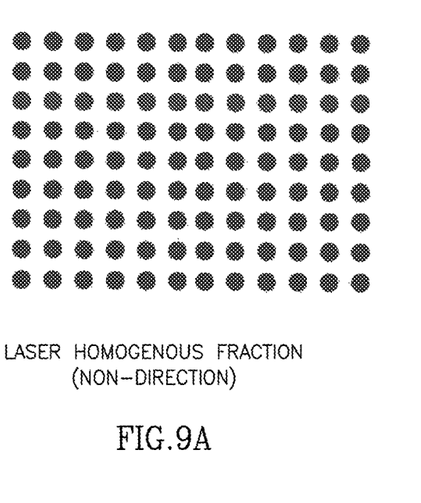
FIG. 9A to 9D illustrate the application of a flat sheet over the area to be treated and the treatment steps.
Figure 9B:
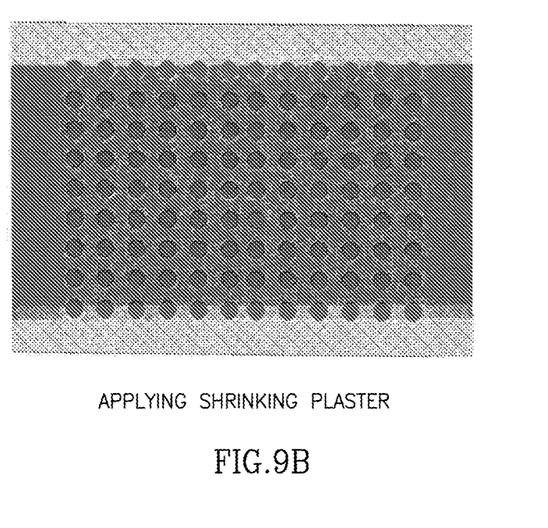
Figure 9C:
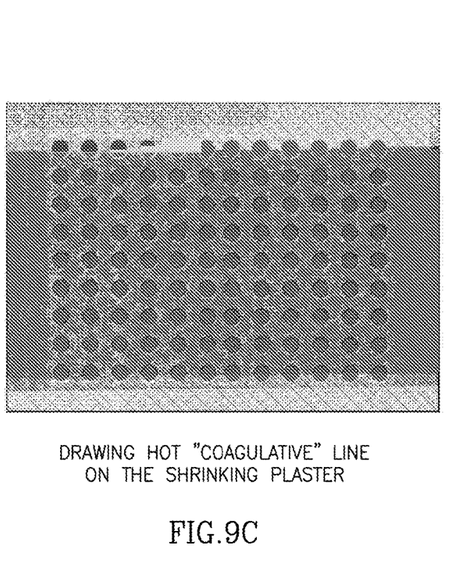
Figure 9D:
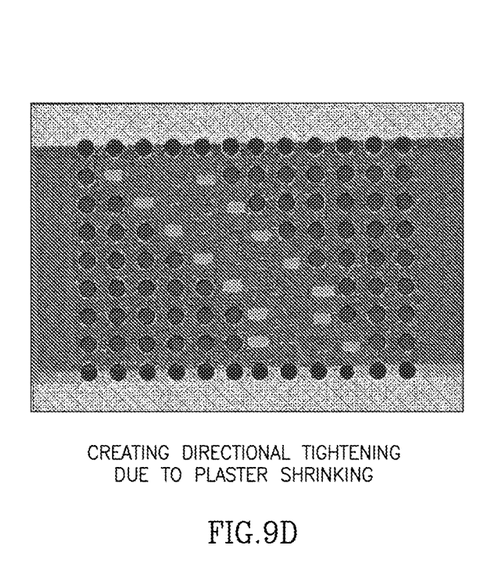

Referring now to FIG. 8, compressed and welded ablative fractional holes 81 are illustrated. These holes were bonded by targeting non-ablative laser spots 82. Since a non-ablative laser may cause local tightening, a non-ablative spot 83 located in-between welded microchannels 84 may re-open these welded microchannels. Therefore, the present invention provides a laser system for directional skin tightening which is configured to lase the non-ablative laser mainly on and in the vicinity to the ablated microchannels to avoid the reopening of bonded microchannels. Due to the same phenomena of local tightening due to non-ablative irradiation, another aspect of the invention is to ablate microchannels 84 between coagulated areas 82 as "strain releasers" for welded microchannels 81. In order to achieve directional tightening along specific directions, and at varying amounts across a larger surface for a desired cosmetic effect, not all of the ablated fractional microchannels may need to be bonded by the non-ablative laser. Non-homogeneous or discrete distribution of welding spots may target only a subset of a microchannel fractional pattern. Moreover, the compression step for compressing an ablated fractional pattern of microchannels may compress all or only a subset set of the ablated microchannels pattern while the welding step again may target only a subset of the compressed microchannels. When the coagulative laser operating at a wavelength of 1,565 nm was applied alone, only coagulative zones could be histologically observed. U.S. application Ser. No. 13/038,773, filed Mar. 2, 2011, which discloses various combinations of ablative and non-ablative laser treatments which may be useful in combination with the present invention, is incorporated herein by reference in its entirety.

Applying the coagulative laser in clinical setup 2 above (at 30 mj) immediately following the ablative treatment resulted in detected closed holes. Although tissue welding was seen to occur following a double pass of the coagulative laser, a single pass appeared to achieve the same result. Since the scanned coagulative laser on skin surface was performed randomly, a few ablated, non-welded holes could be detected as not all area was covered homogeneously by the non-ablative coagulative laser in the evaluated scanning setups.

When free fiber treatment of the coagulative laser was used to weld the ablated tissue, tissue welding was achieved, as detected by both methodologies, that is, under the binocular microscopy as well as histologically.

The potential of providing a dual wavelength treatment in order to achieve directional tightening was successfully proven in the above study. As seen in the ex-vivo study shown in FIG. 5, round-shaped ablative zones created by CO2 laser have mostly been welded by the subsequent treatment of the non-ablative laser (1,565 nm). Not all ablative zones were welded as the non-ablative energy was randomly distributed over the ablative-treated areas, however, the tendency of tissue welding could be clearly observed. The ablative zones were significantly closed, especially in the deeper parts of evaporated areas. This phenomenon could be seen in both the perpendicular sections and horizontal sections of the in-vivo study of FIG. 3. This effect occurred immediately following treatment procedure. Similar positive results were seen when the non-ablative laser was applied to ablative zones using energy levels of 10 mj and 20 mj as seen in FIG. 3. Energy levels of 30 mj were found to be not desirable due to safety concerns when applied to the ablative zone.

While the above discussion has been directed to the use of a CO2 laser, it is to be understood that the present invention is not so limited and other suitable laser sources may be employed depending on desired effects and results. For example, a YAG laser which may be more ablative and less coagulative than a CO2 laser may be employed to create the microchannels.

Clearly, other sequences of application of the ablative laser and the non-ablative laser may be envisioned, as the present invention is not limited to a sequence of ablate/squeeze/non-ablate (a/k/a heat). For example, the sequence may be squeeze/ablate/heat or ablate/heat/squeeze or heat/ablate/heat/squeeze or any other permutation of the factors of ablating, squeezing and heating.

While, as may be seen in FIG. 1, the ablated/treated area may be squeezed "by hand", the present invention also envisions other methodologies to achieve this squeezing or compressing. One example is a mechanical device that compresses/squeezes the skin tissue to leave the operator's hands free to operate the laser device doing the ablation and/or heating. This may be a freestanding device (like a pair of tweezers or tongs) or may be a device attached to the distal portion of the laser device itself, so that in one motion the skin tissue is approached, the tongs squeeze the skin tissue either before or after firing of the ablative laser pulse(s) in any desired order. While treating only small areas at a time, say approximately 1 cm squares, and with a degree of tightening within this square controlled by the density of the lesions, with higher density providing more tightening, with the immediate effect of the welding, this can be applied to an as needed location, with a real time impact on directional tightening. While the above discusses squeezing or compressing using tweezers or tongs, it is envisioned that an opposing motion—stretching—is also within the purview of the present invention, and is discussed below.

Figure 10A:
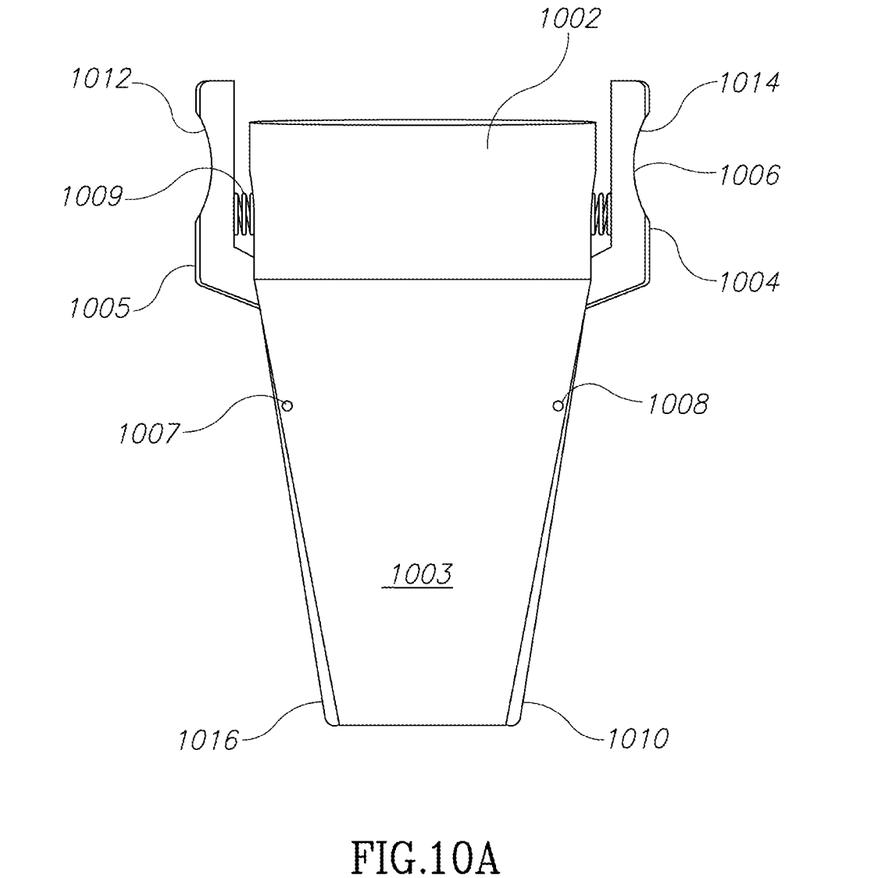
FIGS. 10A, 10B, 10C and 10D illustrate an exemplary mechanical device for either compressing the skin or stretching the skin before, during and/or after a procedure in accordance with the present invention.

Turning now to FIGS. 10A through 10D, these figures illustrate an exemplary mechanism which may be used to either compress the skin tissue or stretch it (or even both). In FIG. 10A, the mechanism 1002 includes a tapered body 1003 (although the body portion may not be tapered) on which is mounted two pivoted arms 1004 and 1005. Although two arms are shown it is to be understood that any number may be employed. The arms 1004 and 1005 are pivoted at points 1008 and 1007 and biased by springs 1006 and 1009. When, by way of example only, pressure is placed on depressions 1012 and 1014 against the action of the springs, the arms will pivot about points 1008 and 1007 and the ends 1010 and 1016 of the arms will move in an outward direction.

Figure 10B:
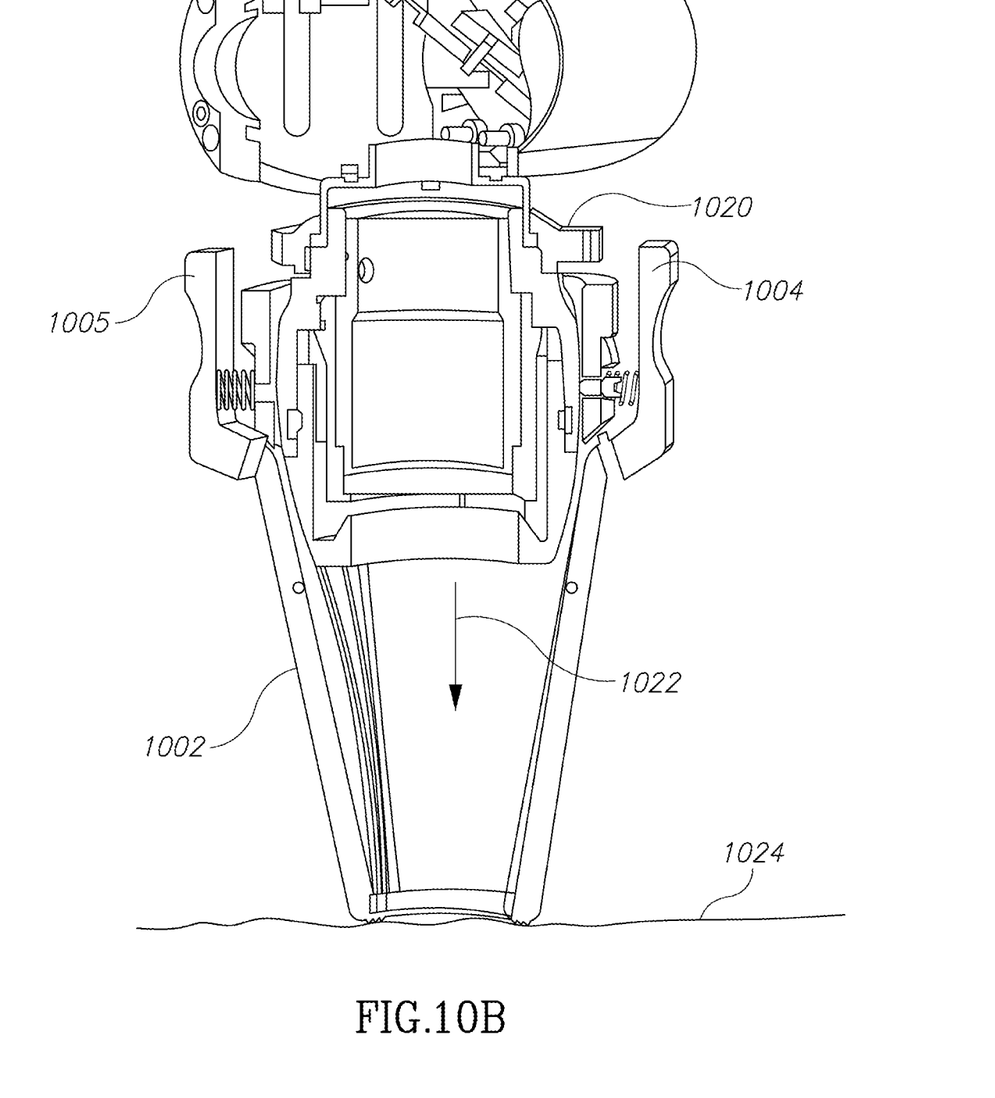
Figure 10C:
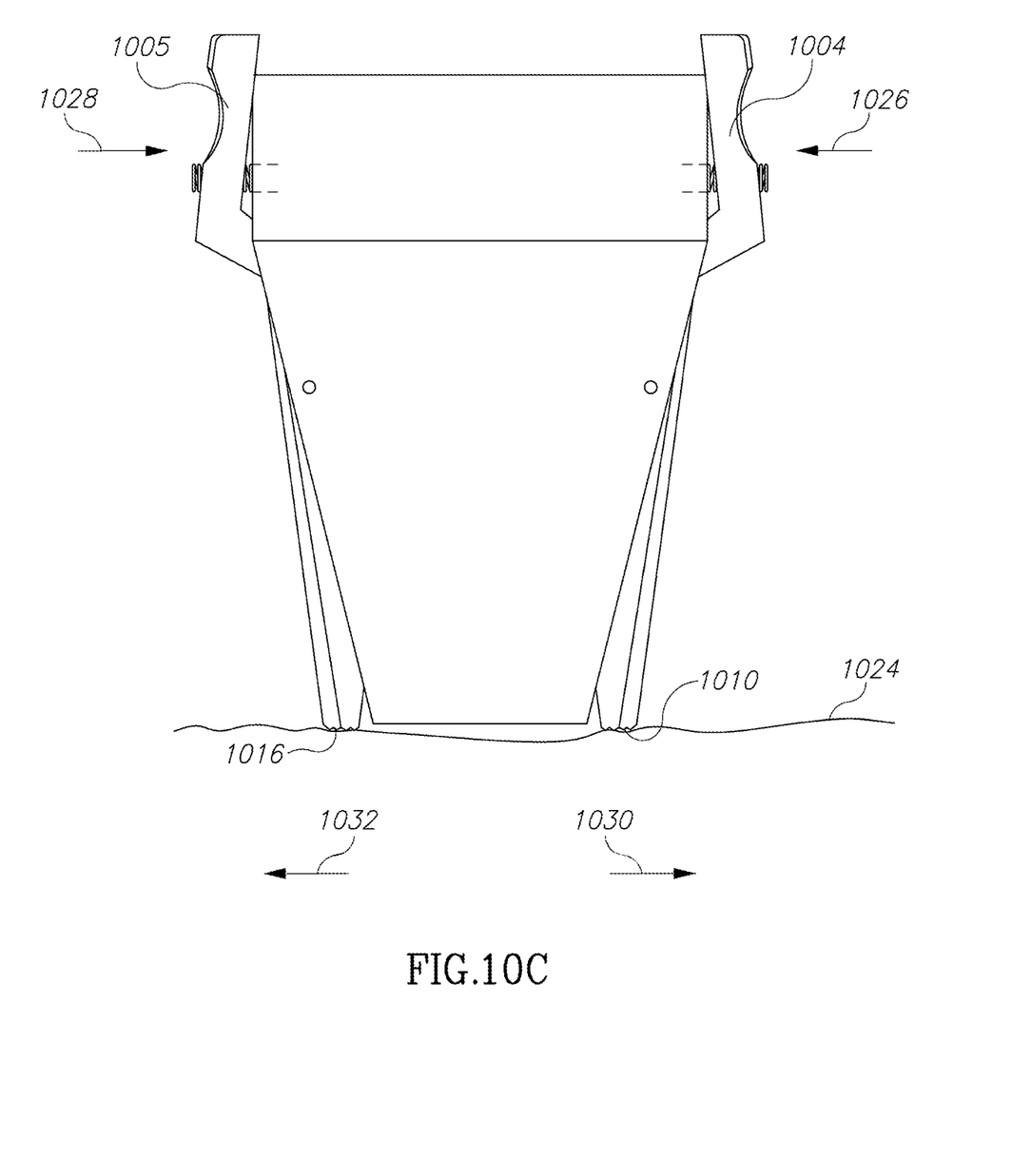

Turning now to FIG. 10B, the mechanism 1002 of FIG. 10A is shown mounted on laser device 1020. It is to be understood that the laser device will be activated and fire along axis and in direction 1022 towards skin tissue surface 1024. In FIG. 10B, the arms 1004 and 1005 are shown in their closed or non-extended positions for this illustration. Turning now to FIG. 10C, this figure shows the arms 1004 and 1005 in the position after the arms have been depressed in directions 1026 and 1028. As can be seen, the ends 1010 and 1016 of the arms have moved in directions 1030 and 1032 along the skin tissue surface 1024.

This, from the above arrangement, it can be seen that two actions may be contemplated. First, the mechanism may contact the skin tissue when the arms are in the position shown in FIG. 10C, and then the act of depressing in directions 1026 and 1028 stopped, which will cause the arms to move to the position of FIG. 10A. This action will cause any skin tissue situated between ends 1010 and 1016 to be squeezed or compressed. This action may occur before, during or after activation of the ablative and/or non-ablative laser(s).

In a second arrangement, the mechanism may contact the skin tissue in the position shown in FIG. 10B and the arms then depressed to move them to the position shown in FIG. 10C while in contact with the skin tissue. This will cause the skin tissue to be stretched in directions 1030 and 1032. This action also may occur before, during or after activation of the ablative and/or non-ablative laser(s).

Figure 10D:
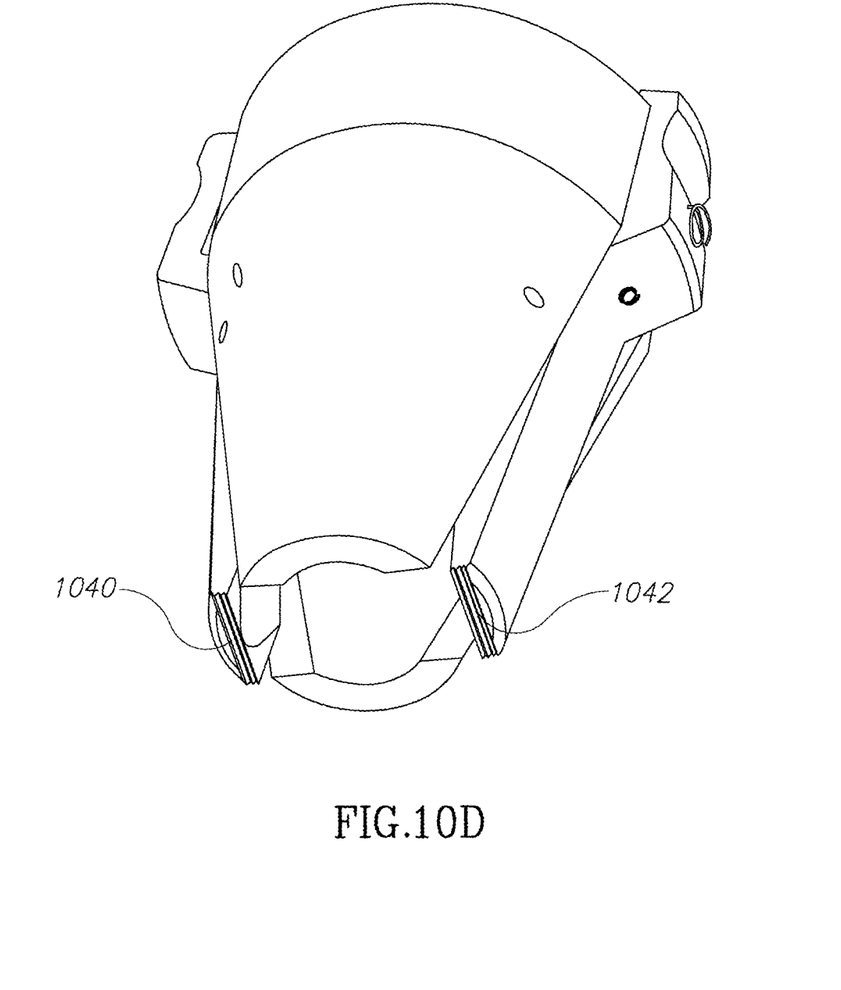

In order that the skin tissue be adequately contacted and gripped for either compressing or stretching, the ends 1010 and 1016 of the arms may have serrations 1040 and 1042 as seen in FIG. 10D to better grip and manipulate the tissue. The body 1003 shown in FIG. 10A may be solid or of a skeleton-like framework and may be of a clear or an opaque material. It may also be of a permanent-type or disposable material.

A programmed controller may be employed in the apparatus and method of the present invention to control the positioning and the operation of the ablative and the non-ablative lasers, the positioning of the non-ablative laser after the operation of the ablative laser as discussed above, and even the movement of the arms 1004 and 1005. The controller may include a display and a user interface, as conventionally employed in cosmetic laser devices, to facilitate the operation of the device.

Another methodology for squeezing the skin is to apply a flat sheet onto the skin tissue to be treated as shown in FIGS. 9A to 9D. The material of the flat sheet may be, by way of example, of polymer and may be either isotropic or anisotropic. When heat is applied to the polymer sheet it will tend to shrink in its length and width dimensions, either uniformly (in the case of an isotropic polymer) or non-uniformly (in the case of an anisotropic polymer). This shrinkage will cause any microchannels ablated in a previous step to move from a round hole to closed, oval holes. The sequence of events is illustrated in FIGS. 9a through 9D. The choice of an isotropic or anisotropic polymer allows the ability to directionally tighten the skin tissue as desired for the particular treatment regimen. It is also envisioned that the flat sheet may be placed onto the patient's skin tissue, the ablative laser caused to fire through the flat sheet to ablate microchannels and then a non-ablative laser applied to cause shrinkage of the sheet and thus closing of the ablated microchannels.

As an alternative, instead of a sheet which may compress the skin tissue in one or more directions, a flat sheet may be employed to simply hold or maintain the tissue in its condition after a procedure during which the skin was compressed (or for that matter stretched) by either manual compression or stretching or manipulation of the skin tissue through the mechanical device of FIGS. 10A through 10D.

In addition, once the ablation/heating steps have occurred as described above, in order to accelerate the "welding" of the microchannels shut, a cold compress or cooled surface may be pressed onto the treated site.

The tendency of tissue welding with non-ablative laser was seen also when applied to the line-shape ablative zones. These results were seen in both, perpendicular and horizontal sections. However, only non-ablative energy level of 10 mj was safe when it was applied to the line-shape ablation, when 20 mj was considered to be inappropriate for reasons of safety.

The initial feasibility study to create ablated zones and then adhere the margins by using a non-ablative laser was successfully achieved.

In addition, the ability to weld the skin tissue of a several hundred microns incision has a higher successful potential than welding of deep and long incisions.

What we claim is:

1. A cosmetic method of directionally tightening human skin tissue comprising the steps of:
    (a) providing an ablative laser source and a non-ablative laser source;
    (b) using the ablative laser source to form one or more microchannels in the skin tissue;
    (c) using the non-ablative laser source to selectively weld one or more of the microchannels, wherein the selective welding causes the skin tissue to tighten in one or more directions.

2. The cosmetic method of claim 1, further comprising the step of (d) squeezing or stretching the skin tissue in the one or more directions across a portion of the skin tissue treated or along a portion of the skin tissue treated.

3. The cosmetic method of claim 2, wherein the skin tissue treated is one or more wrinkles and the step of (d) squeezing or stretching is across the one or more wrinkles or along the long axis of the one or more wrinkles.

4. The cosmetic method of claim 1, wherein the wavelength of the ablative laser is about 10,600 nm or about 2940 nm.

5. The cosmetic method of claim 1, wherein the wavelength of the non-ablative laser ranges from about 1400-1565 nm.

6. The cosmetic method of claim 1, wherein the step of (d) squeezing or stretching is performed with a mechanical squeezer or stretcher.

7. The cosmetic method of claim 6, wherein the mechanical squeezer or stretcher comprises a body portion, the body portion having a plurality of arms, wherein the arms have end portions which are movable towards and away from one another, further comprising the steps of contacting the skin tissue with the end portions of the arms and manipulating the end portions in contact with the skin tissue to either move towards one another or move away from one another, thereby either squeezing or stretching the skin tissue.

8. The cosmetic method of claim 1, wherein step (b) takes place before step (c).

9. The cosmetic method of claim 2, wherein the step of squeezing or stretching is performed after step (b).

* * * * *